(12) United States Patent
Langley et al.

(10) Patent No.: US 7,985,201 B2
(45) Date of Patent: Jul. 26, 2011

(54) RELATING IN AND RELATING TO AN INJECTION DEVICE

(75) Inventors: Christopher Nigel Langley, Leamington Spa (GB); Robert Woolston, Moreton Morrell (GB); David Aubrey Plumptre, Droitwich (GB)

(73) Assignee: DCA Design International Limited, Warwick (GB)

( * ) Notice: Subject to any disclaimer, the term of this patent is extended or adjusted under 35 U.S.C. 154(b) by 2377 days.

(21) Appl. No.: 10/471,692

(22) PCT Filed: Mar. 26, 2002

(86) PCT No.: PCT/GB02/01418
§ 371 (c)(1),
(2), (4) Date: Sep. 15, 2003

(87) PCT Pub. No.: WO02/076535
PCT Pub. Date: Oct. 3, 2002

(65) Prior Publication Data
US 2004/0087904 A1    May 6, 2004

(30) Foreign Application Priority Data
Mar. 27, 2001 (GB) .................................. 0107601.7

(51) Int. Cl.
*A61M 37/00* (2006.01)

(52) U.S. Cl. ........................................................ 604/131

(58) Field of Classification Search .................. 604/131, 604/135, 224, 207–210, 152–155; 128/DIG. 1, 128/DIG. 12
See application file for complete search history.

(56) References Cited

U.S. PATENT DOCUMENTS

| 5,637,095 A | 6/1997 | Nason et al. |
| 6,110,149 A | 8/2000 | Klitgaard et al. |
| 6,537,251 B2 * | 3/2003 | Klitmose ...................... 604/135 |
| 6,796,970 B1 * | 9/2004 | Klitmose et al. .............. 604/207 |

FOREIGN PATENT DOCUMENTS

| WO | WO 98/57688 | 12/1998 |
| WO | WO 01/78812 A1 | 10/2001 |

* cited by examiner

*Primary Examiner* — Matthew F Desanto
(74) *Attorney, Agent, or Firm* — Oliff & Berridge, PLC

(57) ABSTRACT

Injection devices are known for the self administration of a medicament by patients in which the medicament is contained within a cartridge located within the injection device. It is a problem that such injection devices should be small enough to fit into a jacket pocket or a hand bag without difficulty. Concurrently, the injection device must be of size that enables a piston or similar used to drive a cartridge bung within the cartridge to be moved both to a maximum dispense position within the cartridge and to be fully withdrawn from the cartridge to allow for replacement of the cartridge. A drive mechanism for an injection device is disclosed comprising a piston member 10, a semi rigid belt 18 connected to the piston member 10, a belt drive means to selectively engage with the semi rigid belt 18 to drive the semi rigid belt 18, and a dose setting mechanism to control the selective engagement of the semi rigid belt in which the semi rigid belt 18 includes a track incorporated therein and the belt drive means comprises a tooth 50 for selective engagement with the track to drive the belt 18 only when there is relative movement between the semi rigid belt 18 and the tooth 50 in a first direction. An injection device comprising such a drive mechanism is also disclosed.

11 Claims, 2 Drawing Sheets

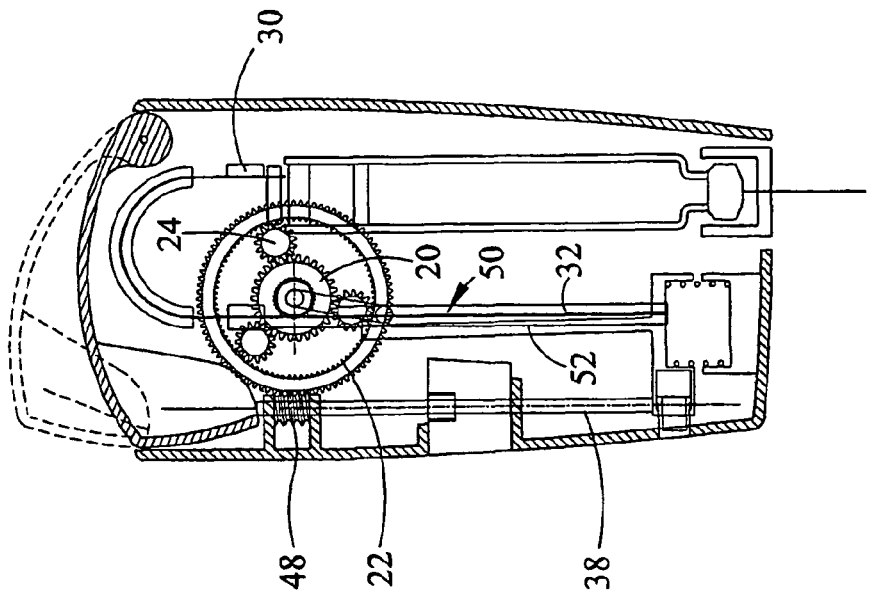
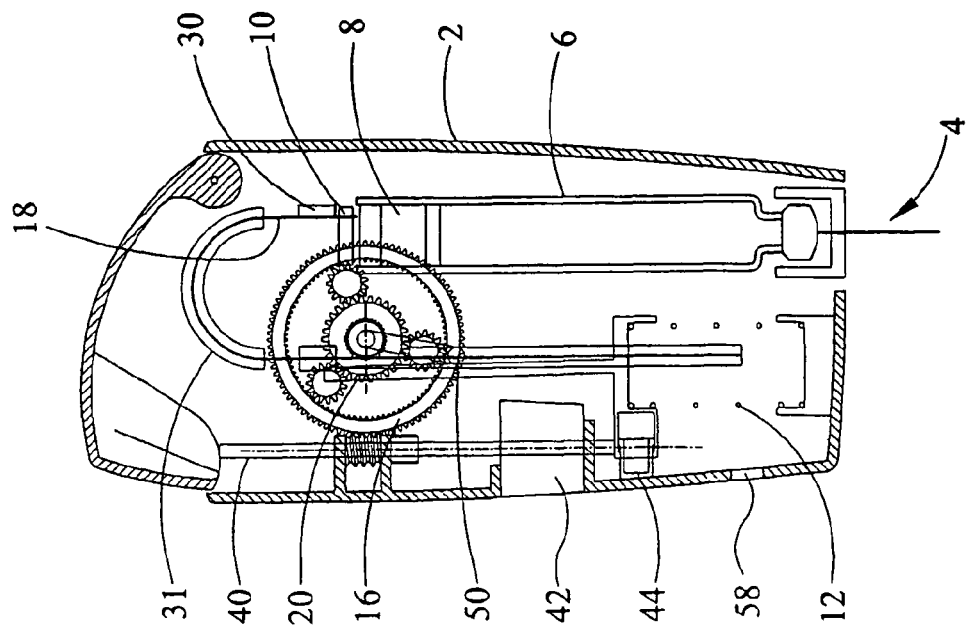

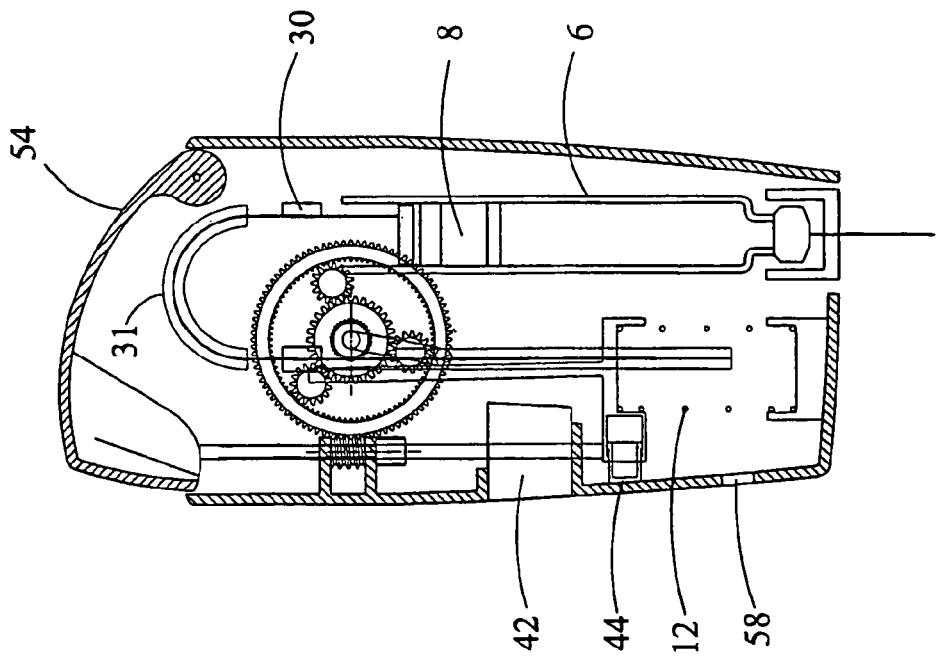
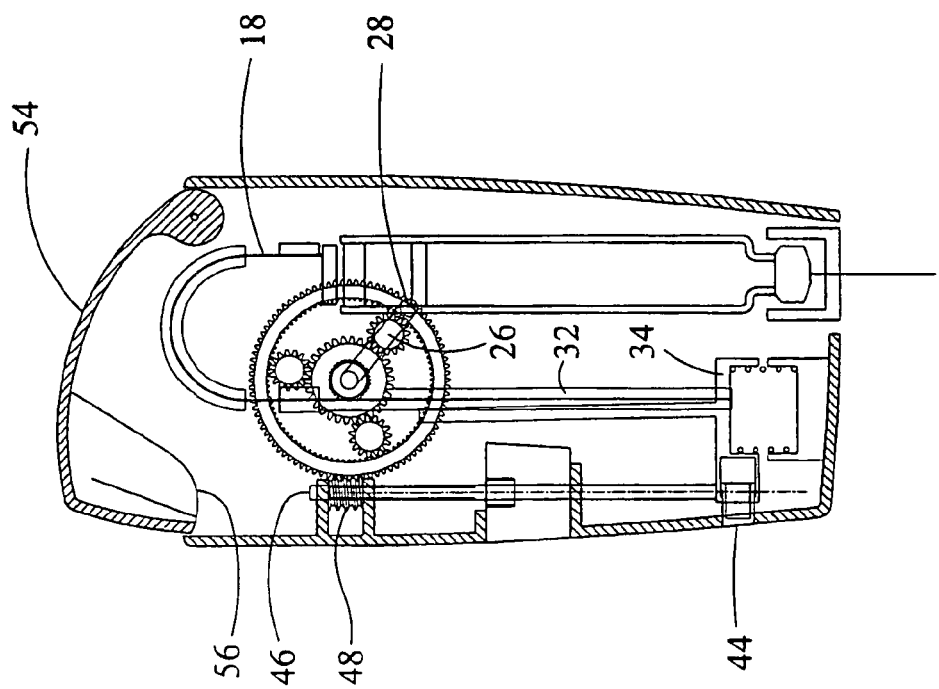

RELATING IN AND RELATING TO AN INJECTION DEVICE

The present invention relates to improvements in an injection device, and in particular to improvements in a portable injection device for dispensing controlled quantities of a medicament.

Injection devices are known for the self administration of a medicament by patients. For example, those suffering from diabetes may require regular injections of insulin, others may require regular injections of a growth hormone. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the infirm, those suffering from vision difficulties and those suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

U.S. Pat. No. 6,110,149 discloses a drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, in which the drive mechanism comprises a piston member, a semi rigid belt including a track incorporated therein connected to the piston member, a belt drive means to drive the semi rigid belt, and a dose setting mechanism to control the selective engagement of the semi rigid belt. This provides one solution to the problems noted.

It is an advantage of the present invention that it provides another solution to these conflicting requirements.

According to a first aspect of the present invention, a drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge is disclosed, in which the drive mechanism comprises a piston member, a semi rigid belt including a track incorporated therein connected to the piston member, a belt drive means to drive the semi rigid belt, and a dose setting mechanism to control the selective engagement of the semi rigid belt characterised in that the belt drive means selectively engages with the semi rigid belt and in that the belt drive means comprises a tooth for selective engagement with the track to drive the belt only when there is relative movement between the semi rigid belt and the tooth in a first direction.

Preferably, the belt drive means further comprises an inner gear adapted to engage with the track in the semi rigid belt and be driven by movement of the track in the first direction.

Preferably, the belt drive means further comprises a flexible member to carry the tooth, a second piston member to carry the flexible member and a charge means to drive the belt drive means in the first direction. More preferably, the charge means comprises a spring.

Preferably, the second piston member includes a biased dose button adapted releasably to retain a dosing spindle in a desired position.

Preferably, the dose setting mechanism comprises a dial dose means, a dosing spindle, an outer gear, an outer gear drive means located between the spindle and the outer gear, a plurality of intermediate gears interposed between the inner gear and the outer gear, and a dose trip peg carried by one of the plurality of intermediate gears to control the selective engagement of the semi rigid belt.

Preferably the dose setting mechanism further comprises displacement means to displace the dosing spindle.

Preferably, the semi rigid belt and the piston member are formed as a unitary component.

According to a second aspect of the present invention, an injection device having a housing is characterised in that the device further comprises a drive mechanism according to the first aspect of the present invention.

Preferably, the displacement means comprises a button located for displacement within the housing of the injection device.

Preferably, the housing has an aperture for cooperation with the or a dose button.

The invention will now be described, by way of example only, with reference to the accompanying drawings in which:—

FIG. 1 shows a side section of an injection device having a drive mechanism according to the present invention in which the injection device is closed and a medicament cartridge is full;

FIG. 2 shows a side section similar to FIG. 1 with the injection device ready for use;

FIG. 3 shows a side section similar to FIG. 1 with a dosage of medicament dialled; and FIG. 4 shows a side section similar to FIG. 1 with the dosage delivered.

Like reference numerals will be used to refer to like parts of the injection device.

Referring first to FIG. 1 there may be seen an injection device in accordance with the present invention. The injection device comprises a main housing 2 and a drive mechanism. A needle unit 4 including a delivery member in the form of a hollow needle is secured to a first end of the main housing 2. A medicament cartridge 6 having a first end and a second end may be stored in the main housing 2. When the needle unit 4 is in place, the needle unit 4 pierces a flexible membrane at the first end of the medicament cartridge 6. A displaceable bung 8 is located at the second end of the medicament cartridge 6. A cover (not shown) may be provided over the first end of the main housing 2 to protect the needle unit 4 from damage and a user from inadvertent pricking by the needle. The cover also provides a discrete appearance for the injection device.

The drive mechanism comprises a piston member 10, a semi-rigid belt 18 connected to the piston member 10, a belt drive means to selectively engage with the semi-rigid belt 18 to drive the semi-rigid belt 18, and a dose setting mechanism to control the selective engagement of the semi-rigid belt 18. The semi rigid belt 18 may comprise any suitable material, for example spring steel or a plastics material. Where the semi rigid belt and the piston member are formed from a plastics material, they may be formed as a unitary component.

The piston member 10 is located adjacent the bung in the medicament cartridge 6. The piston member 10 is connected to a first end of the semi-rigid belt 18. Guide means are provided in the main housing 2 to direct the semi-rigid belt 18. In the illustrated embodiment, first, second and third guide means are shown. The first guide means 30 is located towards the first end of the semi-rigid belt 18 to direct the piston member 10 towards the first end of the medicament cartridge 6. The second guide means 31 is substantially U-shaped. The third guide means 32 is located substantially parallel to and adjacent with the medicament cartridge 6.

The semi-rigid belt 18 is provided along a portion of its length with a track. Conveniently, the track takes the form of a series of openings which may be selectively engaged by the belt drive means. The track is also engaged by a first part of an inner gear 20 of a planetary gear arrangement. The planetary gear arrangement further comprises an outer gear 22 and a plurality of intermediate planetary gears 24 located between a second part of the inner gear 20 and an inner track on the outer gear 22. A dose trip peg 26 is adapted to rotate about a first end. In use, the first end is carried from a central shaft of the inner gear 20. The dose trip peg 26 is also carried from one of the intermediate planetary gears 24. Thus, as the intermediate planetary gears 24 precess about the inner gear 20, the dose trip peg 26 is caused to rotate about the first end. A second end of the dose trip peg 26 is provided with a finger or tab 28 the purpose of which is described below.

The outer gear 22 is also provided with an outer track. The outer track engages with a worm gear 48 forming a part of the dose setting mechanism.

The worm gear 48 is located within the housing 2 by first and second lugs.

A dosing spindle 38 is provided with a spline 40 at a first end thereof. The spline 40 passes through the worm gear 48 to drive the worm gear 48. The dosing spindle 38 passes through a dose dial means 42. Operation of the dose dial means 42 causes rotation of the dosing spindle 38 and the associated spline 40.

A charge spring 12 is provided between a first end of the main housing 2 and a second piston member 34. The main housing 2 and the second piston member 34 are preferably each provided with a suitably shaped recess to locate and to retain the charge spring 12.

The second piston member 34 is located between the charge spring 12 and a first end of the dosing spindle 38. The second piston member 34 includes a slidable biased dose button 44 retained within a suitable bore provided in the second piston member 34.

The second piston member 34 additionally comprises a flexible member 52. The flexible member 52 is connected at a first end to the second piston member 34 and is provided at an second end with a dog tooth 50. The flexible member 52 is biased towards the semi-rigid belt 18.

A second end of the dose setting spindle 38 is provided with an abutment surface 46.

A cap or button 54 is provided adapted for movement with respect to the main housing 2. In the illustrated embodiment, the button 54 is adapted for pivoting movement with respect to the main housing 2. The button 54 is provided with a stop member 56 extending from an underside of the button 54. The stop member 56 may take the form of a web extending from an underside of the button 54.

In FIG. 1, the injection device is in a closed or off condition. The abutment surface of the dosing spindle 38 is in abutment with the stop member 56 of the button 54. The dose button 44 is retained within the second piston member 34 against an inner wall of the main housing 2. The dose button 44 is biased towards the inner wall of the main housing 2. The finger or tab 28 of the dose trip peg 26 is in contact with the flexible member 52 to hold the dog tooth 50 apart from the track in the semi rigid belt 18.

In order to operate the device, a user first depresses the button 54. The stop member 56 then causes the dosing spindle 38 to be displaced towards a first end of the main housing 2. This causes the first end of the dosing spindle 38 to displace the second piston member 34 towards the first end of the housing 2 thereby compressing the charge spring 12. When the button 54 has been fully depressed, the dose button 44 enters into alignment with and passes through an opening 58 provided in a wall of the main housing 2. This retains the second piston member 34 in the same position relative to the main housing 2 until the dose button 44 is pushed back through the opening. The button 54 may be biased such that when the dosing spindle 26 has been displaced the button 54 reverts to the closed position (FIG. 2).

The user now uses the dial dose means 42 to set the required dose. This causes rotation of the dose setting spindle 26 thereby driving the outer gear 22 through the worm gear 48. The inner gear 20 and the piston member 10 remain stationery during this operation. Due to the relative motion of the outer gear 22 with respect to the inner gear 20 the intermediate planetary gears 24 are caused to rotate about the inner gear 20. This causes the dose trip peg 26 to rotate about the first end. Thus, the angular displacement of the dose trip peg 26 is proportionate to the dose that is dialled by a user.

Dialling of the dose causes the finger or tab 28 of the dose trip peg 26 to move away from the flexible member 52 allowing the dog tooth 50 to come into contact with the track in the semi rigid belt 18. It will be understood that the dog tooth 50 may enter through one of the openings in the track or abut a portion of the semi rigid belt intermediate adjacent openings in the track (FIG. 3).

The dose button 44 is then depressed out of engagement with the opening 58. The charge spring 12 then drives the second piston member 34 away from the first end of the main housing 2. The flexible member 52 is driven towards a second end of the main housing. The dog tooth 50 is moved into engagement with an edge of the current opening (or next opening if adjacent an intermediate belt portion). The semi rigid belt 18 is then driven by the movement of the second piston member 34 causing the piston member 10 to be driven into the bung 8 to drive the bung 8 towards the second end of the medicament cartridge 6. As the semi rigid belt 18 is driven, the semi rigid belt 18 drives the first part of the inner gear 20 thereby rotating the dose trip peg 26 back towards the flexible member 50. When the finger or tab of the dose trip peg 26 displaces the dog tooth 50 from the semi rigid belt 18, the semi rigid belt 18 is no longer driven by the dog tooth 50 and further movement of the second piston member 34 has no effect upon the piston member 10 (FIG. 4) The second piston member 34 then only acts to return the dosing spindle 38 and the associated spline 40 to the position shown in FIG. 1.

This process may be repeated until the medicament cartridge 6 is empty, the medicament cartridge 6 contains insufficient medicament to deliver the dialled dose or some other condition is met. The piston member 10 may then be withdrawn to allow replacement of the medicament cartridge 6. For example, the inner gear 20 may be driven to return the semi rigid belt 18 to the position shown in FIG. 1. It will be understood that the dog tooth 50 may be so shaped as to allow passage of the semi rigid belt 18 in a first direction but to engage the track when the semi rigid belt 18 is moved in an opposite direction.

The relative arrangement of the drive mechanism and the medicament cartridge means that the main housing provides a relatively large flat face where a relatively large dose display, such as a liquid crystal display may be located. This in turn enables the dose display to use relatively large figures or other characters. This is an advantage for those with impaired vision.

The invention claimed is:

1. A drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, in which the drive mechanism comprises a piston member, a semi rigid belt including a track incorporated therein connected to the piston member, a belt drive means to drive the semi rigid belt, and a dose setting mechanism to control the selective engagement of the semi rigid belt is characterised in that the belt drive means selectively engages with the semi rigid belt and in that the belt drive means comprises a tooth for selective engagement with the track to drive the belt only when there is relative movement between the semi rigid belt and the tooth in a first direction.

2. A drive mechanism according to claim 1, wherein the belt drive means further comprises a flexible member to carry the tooth, a second piston member to carry the flexible member and a charge means to drive the belt drive means in the first direction.

3. A drive mechanism according to claim 2, wherein the second piston member includes a biased dose button adapted releasably to retain a dosing spindle in a desired position.

4. A drive mechanism for an injection device according to claim 3, wherein the dose setting mechanism further comprises displacement means to displace the dosing spindle.

5. A drive mechanism according to claim 2, wherein the charge means comprises a spring.

6. A drive mechanism for an injection device according to claim 1, wherein the belt drive means further comprises an inner gear adapted to engage with the track in the semi rigid belt and be driven by movement of the track in the first direction.

7. A drive mechanism for an injection device according to claim 6, wherein the dose setting mechanism comprises a dial dose means, a dosing spindle, an outer gear, an outer gear drive means located between the spindle and the outer gear, a plurality of intermediate gears interposed between the inner gear and the outer gear, and a dose trip peg carried by one of the plurality of intermediate gears to control the selective engagement of the semi rigid belt.

8. A drive mechanism for an injection device according to claim 1, wherein the semi rigid belt and the piston member are formed as a unitary component.

9. An injection device having a housing, wherein the device further comprises a drive mechanism in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, in which the drive mechanism comprises a piston member, a semi rigid belt including a track incorporated therein connected to the piston member, a belt drive means to drive the semi rigid belt, and a dose setting mechanism to control the selective engagement of the semi rigid belt is characterised in that the belt drive means selectively engages with the semi rigid belt and in that the belt drive means comprises a tooth for selective engagement with the track to drive the belt only when there is relative movement between the semi rigid belt and the tooth in a first direction.

10. An injection device according to claim 9, wherein the displacement means comprises a button located for displacement within the housing of the injection device.

11. An injection device according to claim 9, wherein the housing has an aperture for cooperation with a or the dose button.

* * * * *